(12) United States Patent
Xin et al.

(10) Patent No.: US 12,282,025 B1
(45) Date of Patent: Apr. 22, 2025

(54) RAPID DETECTION METHOD FOR RICIN TOXIN

(71) Applicant: Academy of Military Medical Sciences, Beijing (CN)

(72) Inventors: Wenwen Xin, Beijing (CN); Jiaxin Li, Beijing (CN); Lin Kang, Beijing (CN); Tingting Liu, Beijing (CN); Lina Dong, Beijing (CN); Shan Gao, Beijing (CN); Jinglin Wang, Beijing (CN)

(73) Assignee: Academy of Military Medical Sciences, Beijing (CN)

( * ) Notice: Subject to any disclaimer, the term of this patent is extended or adjusted under 35 U.S.C. 154(b) by 0 days.

(21) Appl. No.: 18/789,799

(22) Filed: Jul. 31, 2024

(30) Foreign Application Priority Data

Dec. 27, 2023 (CN) .......................... 202311825136.1

(51) Int. Cl.
*G01N 33/68* (2006.01)
*G01N 21/64* (2006.01)
(Continued)

(52) U.S. Cl.
CPC ......... *G01N 33/68* (2013.01); *G01N 21/6428* (2013.01); *G01N 33/54326* (2013.01);
(Continued)

(58) Field of Classification Search
CPC .. G01N 33/68; G01N 21/6428; G01N 33/582; G01N 2021/6432;
(Continued)

(56) References Cited

U.S. PATENT DOCUMENTS 8,536,319 B2 * 9/2013 Schramm ................. C12Q 1/34
536/26.6
10,907,193 B2 * 2/2021 Suliman .................... C12Q 1/68
(Continued)

FOREIGN PATENT DOCUMENTS

CN 101980023 A 2/2011
WO WO-2013175313 A2 * 11/2013 ............... C12Q 1/68

OTHER PUBLICATIONS

Siming Fang, et al., Unimolecular Chemically Modified DNA Fluorescent Probe for One-Step Quantitative Measurement of the Activity of Human Apurinic/ Apyrimidinic Endonuclease 1 in Biological Samples, Analytical Chemistry, 2015, pp. 11952-11956, vol. 87.

(Continued)

*Primary Examiner* — Shafiqul Haq
(74) *Attorney, Agent, or Firm* — Bayramoglu Law Offices LLC

(57) ABSTRACT

A rapid detection method for ricin toxin is provided. The rapid detection method for ricin toxin comprises reacting an adenine-containing oligonucleotide chain substrate labeled with a fluorescent group and a quenching group, a buffer solution, a BSA solution, a to-be-detected sample and sterile water, incubating at a constant temperature, detecting a fluorescence signal value, and determining whether the ricin toxin exists based on a difference between an average value of final fluorescence signal values and an average value of final fluorescence signal values of a negative control; wherein the sample is judged as a positive sample when the average value of the detected final fluorescence signal values is greater than the average value of the final fluorescence signal values of the negative control by +3 times standard deviation.

6 Claims, 11 Drawing Sheets
(8 of 11 Drawing Sheet(s) Filed in Color)
Specification includes a Sequence Listing.

(51) Int. Cl.
  *G01N 33/543* (2006.01)
  *G01N 33/58* (2006.01)
(52) U.S. Cl.
  CPC ... *G01N 33/582* (2013.01); *G01N 2021/6432* (2013.01); *G01N 2021/6439* (2013.01); *G01N 2333/42* (2013.01)
(58) Field of Classification Search
  CPC ....... G01N 2021/6439; G01N 2333/42; G01N 33/54326
  See application file for complete search history.

(56) References Cited

U.S. PATENT DOCUMENTS

| | | |
|---|---|---|
| 2011/0136106 A1 | 6/2011 | Schramm |
| 2012/0252128 A1 | 10/2012 | Lu et al. |
| 2014/0065623 A1* | 3/2014 | Suliman .................. C12Q 1/68 435/6.12 |

OTHER PUBLICATIONS

Longhui Liang, et al., An in vitro depurination activity assay for ricin based on a novel RNA substrate and its application, Chinese Journal of Analytical Chemistry, 2021, pp. 1694-1703, vol. 49 No. 10.

* cited by examiner

SEQUENCE LISTING

```
Sequence total quantity: 29
SEQ ID NO: 1            moltype = DNA  length = 15
FEATURE                 Location/Qualifiers
misc_feature            1..15
                        note = The sequence is synthetized.
source                  1..15
                        mol_type = other DNA
                        organism = synthetic construct
SEQUENCE: 1
aaaaaaaaaa aaaaa                                                        15

SEQ ID NO: 2            moltype = RNA  length = 15
FEATURE                 Location/Qualifiers
misc_feature            1..15
                        note = The sequence is synthetized.
source                  1..15
                        mol_type = other RNA
                        organism = synthetic construct
SEQUENCE: 2
aaaaaaaaaa aaaaa                                                        15

SEQ ID NO: 3            moltype = DNA  length = 15
FEATURE                 Location/Qualifiers
misc_feature            1..15
```

-continued

```
                            note = The sequence is synthetized.
source                      1..15
                            mol_type = other DNA
                            organism = synthetic construct
SEQUENCE: 3
gctctgcagt cgctg                                                         15

SEQ ID NO: 4                moltype = RNA   length = 15
FEATURE                     Location/Qualifiers
misc_feature                1..15
                            note = The sequence is synthetized.
source                      1..15
                            mol_type = other RNA
                            organism = synthetic construct
SEQUENCE: 4
gctctgcagt cgctg                                                         15

SEQ ID NO: 5                moltype = DNA   length = 32
FEATURE                     Location/Qualifiers
misc_feature                1..32
                            note = The sequence is synthetized.
source                      1..32
                            mol_type = other DNA
                            organism = synthetic construct
SEQUENCE: 5
tatatatata gagagagaga gatatatata ta                                      32

SEQ ID NO: 6                moltype = RNA   length = 32
FEATURE                     Location/Qualifiers
misc_feature                1..32
                            note = The sequence is synthetized.
source                      1..32
                            mol_type = other RNA
                            organism = synthetic construct
SEQUENCE: 6
tatatatata gagagagaga gatatatata ta                                      32

SEQ ID NO: 7                moltype = DNA   length = 32
FEATURE                     Location/Qualifiers
misc_feature                1..32
                            note = The sequence is synthetized.
source                      1..32
                            mol_type = other DNA
                            organism = synthetic construct
SEQUENCE: 7
gcgcgcgcgc gagagagaga gagcgcgcgc gc                                      32

SEQ ID NO: 8                moltype = RNA   length = 32
FEATURE                     Location/Qualifiers
misc_feature                1..32
                            note = The sequence is synthetized.
source                      1..32
                            mol_type = other RNA
                            organism = synthetic construct
SEQUENCE: 8
gcgcgcgcgc gagagagaga gagcgcgcgc gc                                      32

SEQ ID NO: 9                moltype =     length =
SEQUENCE: 9
000

SEQ ID NO: 10               moltype =     length =
SEQUENCE: 10
000

SEQ ID NO: 11               moltype =     length =
SEQUENCE: 11
000

SEQ ID NO: 12               moltype = DNA   length = 12
FEATURE                     Location/Qualifiers
misc_feature                1..12
                            note = The sequence is synthetized.
source                      1..12
                            mol_type = other DNA
                            organism = synthetic construct
SEQUENCE: 12
aaaaaaaaaa aa                                                            12
```

```
SEQ ID NO: 13              moltype = DNA   length = 18
FEATURE                    Location/Qualifiers
misc_feature               1..18
                           note = The sequence is synthetized.
source                     1..18
                           mol_type = other DNA
                           organism = synthetic construct
SEQUENCE: 13
aaaaaaaaaa aaaaaaaa                                                        18

SEQ ID NO: 14              moltype = DNA   length = 21
FEATURE                    Location/Qualifiers
misc_feature               1..21
                           note = The sequence is synthetized.
source                     1..21
                           mol_type = other DNA
                           organism = synthetic construct
SEQUENCE: 14
aaaaaaaaaa aaaaaaaaaa a                                                    21

SEQ ID NO: 15              moltype = DNA   length = 24
FEATURE                    Location/Qualifiers
misc_feature               1..24
                           note = The sequence is synthetized.
source                     1..24
                           mol_type = other DNA
                           organism = synthetic construct
SEQUENCE: 15
aaaaaaaaaa aaaaaaaaaa aaaa                                                 24

SEQ ID NO: 16              moltype = DNA   length = 27
FEATURE                    Location/Qualifiers
misc_feature               1..27
                           note = The sequence is synthetized.
source                     1..27
                           mol_type = other DNA
                           organism = synthetic construct
SEQUENCE: 16
aaaaaaaaaa aaaaaaaaaa aaaaaaa                                              27

SEQ ID NO: 17              moltype = DNA   length = 30
FEATURE                    Location/Qualifiers
misc_feature               1..30
                           note = The sequence is synthetized.
source                     1..30
                           mol_type = other DNA
                           organism = synthetic construct
SEQUENCE: 17
aaaaaaaaaa aaaaaaaaaa aaaaaaaaaa                                           30

SEQ ID NO: 18              moltype = DNA   length = 18
FEATURE                    Location/Qualifiers
misc_feature               1..18
                           note = The sequence is synthetized.
source                     1..18
                           mol_type = other DNA
                           organism = synthetic construct
SEQUENCE: 18
taaaaaaat aaaaaaat                                                         18

SEQ ID NO: 19              moltype = DNA   length = 21
FEATURE                    Location/Qualifiers
misc_feature               1..21
                           note = The sequence is synthetized.
source                     1..21
                           mol_type = other DNA
                           organism = synthetic construct
SEQUENCE: 19
taaataaata aataaataaa t                                                    21

SEQ ID NO: 20              moltype = DNA   length = 24
FEATURE                    Location/Qualifiers
misc_feature               1..24
                           note = The sequence is synthetized.
source                     1..24
                           mol_type = other DNA
                           organism = synthetic construct
SEQUENCE: 20
taataataat aataataata taat                                                 24
```

```
SEQ ID NO: 21          moltype = DNA   length = 18
FEATURE                Location/Qualifiers
misc_feature           1..18
                       note = The sequence is synthetized.
source                 1..18
                       mol_type = other DNA
                       organism = synthetic construct
SEQUENCE: 21
taaataaata ataataat                                                   18

SEQ ID NO: 22          moltype = DNA   length = 18
FEATURE                Location/Qualifiers
misc_feature           1..18
                       note = The sequence is synthetized.
source                 1..18
                       mol_type = other DNA
                       organism = synthetic construct
SEQUENCE: 22
tatatatata tatataat                                                   18

SEQ ID NO: 23          moltype = DNA   length = 16
FEATURE                Location/Qualifiers
misc_feature           1..16
                       note = The sequence is synthetized.
source                 1..16
                       mol_type = other DNA
                       organism = synthetic construct
SEQUENCE: 23
tatagagaga gatata                                                     16

SEQ ID NO: 24          moltype = DNA   length = 20
FEATURE                Location/Qualifiers
misc_feature           1..20
                       note = The sequence is synthetized.
source                 1..20
                       mol_type = other DNA
                       organism = synthetic construct
SEQUENCE: 24
tatatagaga gagatatata                                                 20

SEQ ID NO: 25          moltype = DNA   length = 24
FEATURE                Location/Qualifiers
misc_feature           1..24
                       note = The sequence is synthetized.
source                 1..24
                       mol_type = other DNA
                       organism = synthetic construct
SEQUENCE: 25
tatatataga gagagatata tata                                            24

SEQ ID NO: 26          moltype = DNA   length = 28
FEATURE                Location/Qualifiers
misc_feature           1..28
                       note = The sequence is synthetized.
source                 1..28
                       mol_type = other DNA
                       organism = synthetic construct
SEQUENCE: 26
tatatatata gagagagata tatatata                                        28

SEQ ID NO: 27          moltype = DNA   length = 32
FEATURE                Location/Qualifiers
misc_feature           1..32
                       note = The sequence is synthetized.
source                 1..32
                       mol_type = other DNA
                       organism = synthetic construct
SEQUENCE: 27
tatatatata tagagagaga tatatatata ta                                   32

SEQ ID NO: 28          moltype = DNA   length = 24
FEATURE                Location/Qualifiers
misc_feature           1..24
                       note = The sequence is synthetized.
source                 1..24
                       mol_type = other DNA
                       organism = synthetic construct
SEQUENCE: 28
```

```
tatatatata gagatatata tata                                          24

SEQ ID NO: 29          moltype = DNA   length = 36
FEATURE                Location/Qualifiers
misc_feature           1..36
                       note = The sequence is synthetized.
source                 1..36
                       mol_type = other DNA
                       organism = synthetic construct
SEQUENCE: 29
tatatatata gagagagaga gagagatata tatata                             36
```

RAPID DETECTION METHOD FOR RICIN TOXIN

CROSS REFERENCE TO THE RELATED APPLICATIONS

This application is based upon and claims priority to Chinese Patent Application No. 202311825136.1, filed on Dec. 27, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBRZBC210_Sequence_Listing.xml, created on Jul. 12, 2024, and is 34,620 bytes in size.

TECHNICAL FIELD

The present invention belongs to the technical field of toxin detection, and particularly relates to a rapid detection method for ricin toxin.

BACKGROUND

Ricin toxin (RT) is a toxin protein isolated from *Ricinus communis*, a plant of the genus *Ricinus* in the family Euphorbiaceae. The ricin toxin is extremely toxic and easy to prepare, and has a very similar structure and biological characteristics to abrin toxin (AT). RT can be transmitted through food, water or aerosols, inhibit protein synthesis, and exert toxic effects by causing cell death through direct membrane damage, apoptotic pathways, and cytokine release.

RT is composed of two polypeptide chain subunits, A and B, which are covalently linked by disulfide bonds. The A chain mainly plays a toxic role, while the B chain is non-toxic but can mediate the entry of toxins into cells. Both RT and AT belong to a type II ribosome-inactivating protein (RIP) with N-glycosidase activity, and can specifically and irreversibly hydrolyze adenine (A4324) on the 28S rRNA of the ribosome of an organism, resulting in the inability of the ribosome to bind to an elongation factor, thereby inhibiting the translation function of the ribosome, inhibiting protein synthesis, and then exerting a toxic effect. The enzymatic activity acts on an adenine-containing oligonucleotide chain in vitro, so that adenine is shed and a base deletion site (apurinic/apyrimidinic site, AP Site) is formed at the corresponding position.

The enzymatic activity of toxins not only plays an important role in organisms, but also is also often used as a means of detection. Therefore, RT is usually used to establish a detection method based on its enzymatic activity, which is mainly based on its N-glycosidase activity acting on different types of adenine-containing nucleic acid substrates, and then detecting the adenine content through mass spectrometry technology. This method has the advantages of strong specificity and high sensitivity, and can detect whether RT and AT are toxic or not. However, this method usually takes about 2-5 h from incubation of the toxin and substrate to on-machine detection (the incubation time depends on the toxin content in the sample), which is time-consuming and not conducive to rapid detection. In addition, the used instrument is expensive and costly. In addition, some scholars have achieved the detection of RT by combining an electrochemical sensor, cytotoxicity and other methods, which has a narrow application scope and has not been widely promoted.

Currently, the research on the enzyme properties of RT mainly centers on the activity of N-glycosidase, and the detection method is mainly based on mass spectrometry. If a detection method with high specificity and sensitivity, simple operation, rapid, accurate and efficient detection can be developed based on the enzyme properties other than N-glycosidase of RT, it will help reduce the detection cost, greatly shorten the detection time and achieve rapid on-site detection. Therefore, the detection, identification and characterization of RT in various sample matrices are of great significance.

SUMMARY

In view of this, an objective of the present invention is to provide a rapid detection method for ricin toxin, so as to solve the problems of long time, narrow application range and low sensitivity of the detection method for ricin toxin in the prior art.

In order to achieve the above objective, the present invention provides the following technical solutions.

The present invention provides a detection method for ricin toxin, which comprises the following steps:

Reacting an adenine-containing oligonucleotide chain substrate labeled with a fluorescent group and a quenching group, a buffer solution, a bovine serum albumin (BSA) solution, a to-be-detected sample and sterile water, incubating at a constant temperature, detecting a fluorescence signal value, and determining whether the ricin toxin exists based on a difference between an average value of final fluorescence signal values and an average value of final fluorescence signal values of a negative control; and enriching the to-be-detected sample by using antibody-coated magnetic beads.

Preferably, an amount of the adenine-containing oligonucleotide chain substrate labeled with the fluorescent group and the quenching group, the buffer solution, the BSA solution, the to-be-detected sample and the sterile water is 0.5-6 µL.

Preferably, a coating amount of the antibody and the magnetic beads is 20-30 µg of the antibody-coated 0.5-2 mg of the magnetic beads.

Preferably, the buffer solution comprises an ammonium formate buffer solution, an ammonium acetate buffer solution, an ammonium citrate buffer solution, an ammonium acetate+ethylene diamine tetraacetic acid (EDTA) buffer solution, or an ammonium citrate+EDTA buffer solution.

Preferably, the adenine-containing oligonucleotide chain substrate labeled with the fluorescent group and the quenching group has a final concentration of 2-20 PM, the ammonium formate buffer solution, the ammonium acetate buffer solution and the ammonium citrate buffer solution have a final concentration of 0.2-20 mM; in the ammonium acetate+EDTA buffer solution, the ammonium acetate has a final concentration of 0.2-20 mM, and the EDTA has a final concentration of 0.2-0.8 mM; in the ammonium citrate+EDTA buffer solution, the ammonium citrate has a final concentration of 0.2-20 mM, and the EDTA has a final concentration of 0.2-0.8 mM; and the BSA solution has a final concentration of 10-100 µg/mL.

Preferably, the reaction is performed at a pH value of 3.5-4.8 and a temperature of 40-75° C. for 30-50 min.

Preferably, the fluorescence signal value is detected 2-5 times during the constant temperature incubation.

Preferably, the sample is judged as a positive sample when the average value of the detected final fluorescence signal values is greater than the average value of the final fluorescence signal values of the negative control by +3 times standard deviation.

Compared with the Prior Art, the Present Invention has the Following Beneficial Effects The present invention designs various substrates, and establishes a rapid and efficient RT detection method by optimizing the components, concentration, substrate type, volume, reaction temperature and reaction time of the reaction system. After optimization, the detection method can complete detection only by incubation at the constant temperature of 59° C. for 40 min.

The detection method of the present invention has high sensitivity, the direct addition of the sample into the reaction system can reach the sensitivity of 0.5 µg/mL, the detection after enrichment using antibody-coated magnetic beads can reach the sensitivity of 20 ng/mL with a strong specificity, and no cross reaction exists between the toxin sample and abrin toxin.

The reaction system of the present invention has simple components and reaction conditions, short reaction time and no need for expensive detection instruments and complex professional operation, which breaks through the technical barrier of the current RT detection method, and can be used for on-site rapid screening and rapid detection of in vitro RT poisoning samples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1A:
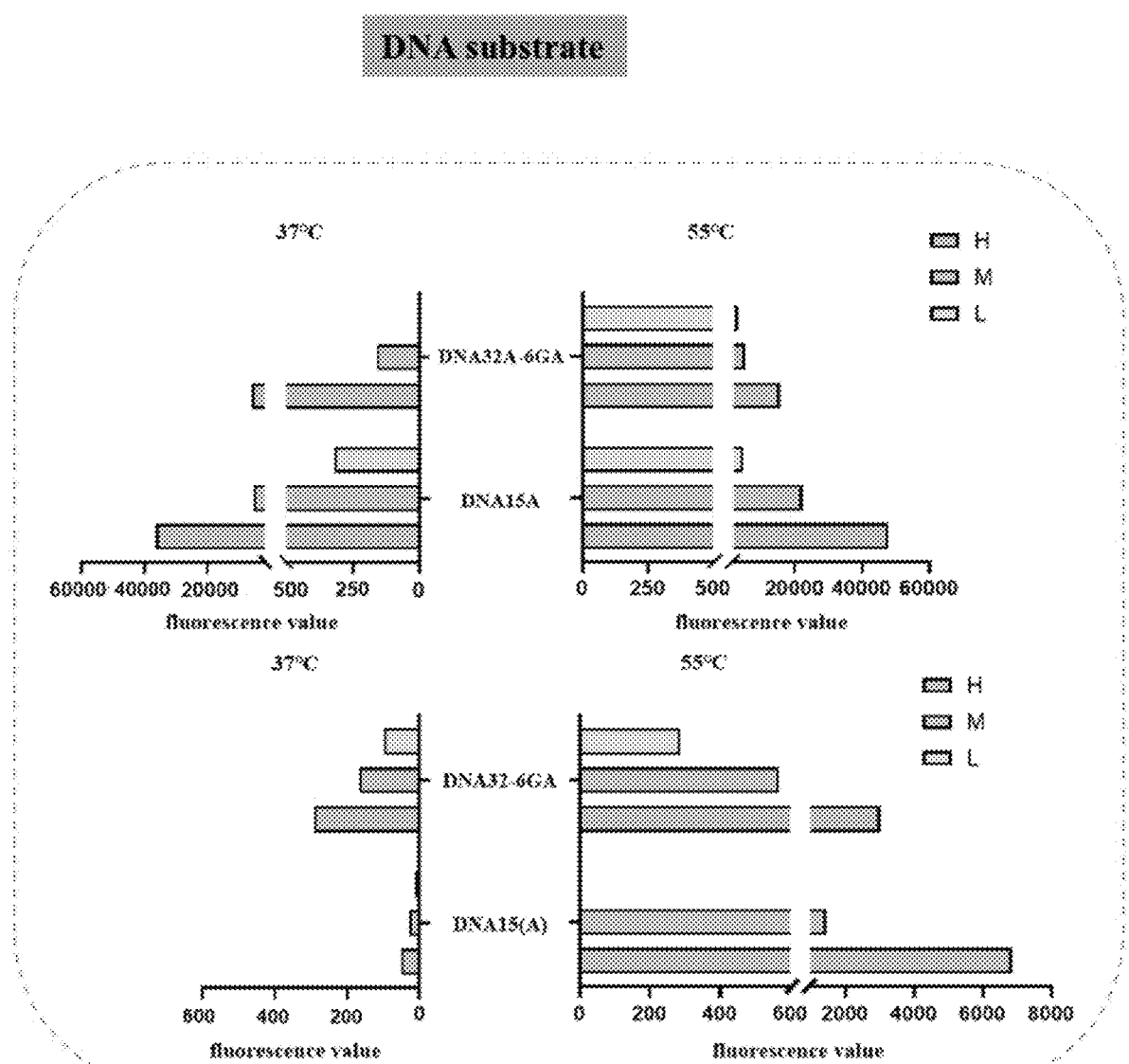
FIGS. 1A-1B are graphs showing the reaction results of RT acting on different single-stranded DNAs and single-stranded RNAs at 37° C. and 55° C. (note: H, 100 µg/mL; M, 10 µg/mL; L, 1 µg/mL)

The present invention provides a detection method for RT, which comprises the following steps:

Reacting an adenine-containing oligonucleotide chain substrate labeled with a fluorescent group and a quenching group, a buffer solution, a BSA solution, a to-be-detected sample and sterile water, incubating at a constant temperature, detecting a fluorescence signal value, and determining whether the RT exists based on a difference between an average value of final fluorescence signal values and an average value of final fluorescence signal values of a negative control; and enriching the to-be-detected sample by using antibody-coated magnetic beads.

In the present invention, the oligonucleotide chain substrate is DNA15A, RNA15A, DNA15(A), RNA15(A), DNA32A-6GA, RNA32A-6GA, DNA32-6GA, and RNA32-6GA; wherein a sequence of the DNA15A is AAAAAAAAAAAAAAA (SEQ ID NO: 1, linear structure);

a sequence of the RNA15A is AAAAAAAAAAAAAAA (SEQ ID NO: 2, linear structure);

a sequence of the DNA15(A) is GCTCTGCAGTCGCTG (SEQ ID NO: 3, the linear chain structure only contains one A);

a sequence of the RNA15(A) is GCUCUGCAGUCGCUG (SEQ ID NO: 4, the linear chain structure only contains one A);

a sequence of the DNA32A-6GA is TATATATATAGAGAGAGAGAGATATATATATA (SEQ ID NO: 5, the stem of the stem-loop structure contains A);

a sequence of the RNA32A-6GA is

```
UAUAUAUAUAGAGAGAGAGAGAUAUAUAUAUA
(SEQ ID NO: 6, the stem of the stem-loop
structure contains A);
``` a sequence of the DNA32-6GA is GCGCGCGCGCGAGAGAGAGAGAGCGCGCGCGC (SEQ ID NO: 7, the stem of the stem-loop structure does not contain A);

a sequence of the RNA32-6GA is GCGCGCGCGCGAGAGAGAGAGAGCGCGCGCGC (SEQ ID NO: 8, the stem of the stem-loop structure does not contain A);

DNA3A, DNA6A, DNA9A, DNA12A, DNA18A, DNA21A, DNA24A, DNA27A, DNA30A, DNA15A3T, DNA15A6T, DNA15A9T, DNA12A6T, DNA9A9T, DNA16-4GA, DNA20-4GA, DNA24-4GA, DNA28-4GA, DNA32-4GA, DNA24-2GA, DNA32A-6GA, and DNA36-8GA, wherein a sequence of the DNA3A is AAA (SEQ ID NO: 9, linear single-stranded DNA);

a sequence of the DNA6A is AAAAAA (SEQ ID NO: 10, linear single-stranded DNA);

a sequence of the DNA9A is AAAAAAAAA (SEQ ID NO: 11, linear single-stranded DNA);

a sequence of the DNA12A is AAAAAAAAAAAA (SEQ ID NO: 12, linear single-stranded DNA);

a sequence of the DNA18A is AAAAAAAAAAAAAAAAAA (SEQ ID NO: 13, linear single-stranded DNA);

a sequence of the DNA21A is AAAAAAAAAAAAAAAAAAAAA (SEQ ID NO: 14, linear single-stranded DNA);
a sequence of the DNA24A is AAAAAAAAAAAAAAAAAAAAAAAA (SEQ ID NO: 15, linear single-stranded DNA);
a sequence of the DNA27A is AAAAAAAAAAAAAAAAAAAAAAAAAAA (SEQ ID NO: 16, linear single-stranded DNA);
a sequence of the DNA30A is AAAAAAAAAAAAAAAAAAAAAAAAAAAAAA (SEQ ID NO: 17, linear single-stranded DNA);
a sequence of the DNA15A3T is TAAAAAAAATAAAAAAAT (SEQ ID NO: 18, with a constant number of A and an increased number of T);
a sequence of the DNA15A6T is TAAATAAATAAATAAATAAAT (SEQ ID NO: 19, with a constant number of A and an increased number of T);
a sequence of the DNA15A9T is TAATAATAATAATAATAATAAT (SEQ ID NO: 20, with a constant number of A and an increased number of T);
a sequence of the DNA15A3T is TAAAAAAAATAAAAAAAT (SEQ ID NO: 18, with an unchanged length and an increased number of T);
a sequence of the DNA12A6T is TAAATAAATAATAATAAT (SEQ ID NO: 21, with an unchanged length and an increased number of T);
a sequence of the DNA9A9T is TATATATATATATATAAT (SEQ ID NO: 22, with an unchanged length and an increased number of T);
a sequence of the DNA16-4GA is TATAGAGAGAGA-TATA (SEQ ID NO: 23, the loop size of the stem-loop structure remains unchanged while the stem length increases);
a sequence of the DNA20-4GA is TATATAGAGAGAGATATATA (SEQ ID NO: 24, the loop size of the stem-loop structure remains unchanged while the stem length increases);
a sequence of the DNA24-4GA is TATATATAGAGAGAGATATATATA (SEQ ID NO: 25, the loop size of the stem-loop structure remains unchanged while the stem length increases);
a sequence of the DNA28-4GA is TATATATATAGAGAGAGATATATATATA (SEQ ID NO: 26, the loop size of the stem-loop structure remains unchanged while the stem length increases);
a sequence of the DNA32-4GA is TATATATATATAGAGAGAGATATATATATATA (SEQ ID NO: 27, the loop size of the stem-loop structure remains unchanged while the stem length increases);
a sequence of the DNA24-2GA is TATATATATAGAGA-TATATATATA (SEQ ID NO: 28, the stem length of the stem-loop structure remains unchanged while the loop size increases);
a sequence of the DNA28-4GA is TATATATATAGAGAGAGATATATATATA (SEQ ID NO: 26, the stem length of the stem-loop structure remains unchanged while the loop size increases);
a sequence of the DNA32A-6GA is TATATATATAGAGAGAGAGAGATATATATATA (SEQ ID NO: 5, the stem length of the stem-loop structure remains unchanged while the loop size increases); and a sequence of the DNA36-8GA is

```
TATATATATAGAGAGAGAGAGAGAGATATATATATA
(SEQ ID NO: 29, the stem length of the stem-
loop structure remains unchanged while the
loop size increases).
```

In the present invention, the fluorescent group is preferably a FAM fluorescent group; the quenching group is preferably a BHQ1 quenching group; the coating amount of the antibody and the magnetic beads is preferably 20-30 μg of the antibody-coated 0.5-2 mg of the magnetic beads, more preferably 22-28 μg of antibody-coated 0.8-1.8 mg of magnetic beads, and further preferably g of antibody-coated 1 mg of magnetic beads; the use amount of the magnetic beads of each to-be-detected sample is preferably 40-60 μg, more preferably 42-58 μg, and further preferably 50 μg; the amount of the adenine-containing oligonucleotide chain substrate labeled with the fluorescent group and the quenching group, the buffer solution, the BSA solution, the to-be-detected sample and the sterile water is preferably 0.5-6 μL, more preferably 0.8-5 μL, and further preferably 1 μL; the buffer solution comprises an ammonium formate buffer solution, an ammonium acetate buffer solution, an ammonium citrate buffer solution, an ammonium acetate+EDTA buffer solution, or an ammonium citrate+EDTA buffer solution, and the buffer solution is preferably the ammonium citrate buffer solution; the final concentration of the adenine-containing oligonucleotide chain substrate labeled with the fluorescent group and the quenching group is preferably 2-20 μM, more preferably 4-15 μM, and further preferably 10 μM; the final concentration of the ammonium formate buffer solution, the ammonium acetate buffer solution and the ammonium citrate buffer solution is preferably 0.2-20 mM, more preferably 0.3-18 mM and further preferably 0.5 mM; in the ammonium acetate+EDTA buffer solution, the final concentration of the ammonium acetate is preferably 0.2-20 mM, more preferably 0.3-18 mM and further preferably 0.5 mM, and the final concentration of the EDTA is preferably 0.2-0.8 mM, more preferably 0.3-0.7 mM and further preferably 0.5 mM; in the ammonium citrate+EDTA buffer solution, the final concentration of the ammonium citrate is preferably 0.2-20 mM, more preferably 0.3-18 mM and further preferably 0.5 mM, and the final concentration of the EDTA is preferably 0.2-0.8 mM, more preferably 0.3-0.7 mM and further preferably 0.5 mM; the final concentration of the BSA solution is preferably 10-100 μg/mL, more preferably 15-80 μg/mL, and further preferably 20 μg/mL; the pH value of the reaction is preferably 3.5-4.8, more preferably 3.8-4.6, and further preferably 4.0; the reaction temperature is preferably 40-75° C., more preferably 50-70° C., and further preferably 59° C.; the reaction time is preferably 30-50 min, more preferably 35-45 min, and further preferably 40 min; the fluorescence signal value is preferably detected 2-5 times during the constant temperature incubation, and more preferably 4 times; and the sample is judged as a positive sample when the average value of the detected final fluorescence signal values is greater than the average value of the final fluorescence signal values of the negative control by +3 times standard deviation.

The technical solutions provided by the present invention will be described in detail below with reference to examples, which, however, should not be construed as limiting the scope of the present invention.

Main Reagents and Instruments:

(1) Main Reagents

Dynabeads™ antibody coupling kit (14311D): Thermo Fisher Scientific Inc.; bovine serum albumin (B2064), ammonium citrate (25102), ammonium formate (70221), and ammonium acetate (73594): Sigma-Aldrich; 0.5 M EDTA (pH 8.0) (E1170): Beijing Solarbio Science & Technology Co., Ltd.; and all oligonucleotide substrates are synthesized by GenScript Biotech Corporation.

(2) Main Instruments

Biological safety cabinet: NUASE, USA; Vortex mixer: Haimen Kylin-Bell Lab Instruments Co., Ltd., Jiangsu; PCR workstation (Air Clean600 PCR Workstation): AirClean Systems, USA; HulaMixer™ sample mixer (15920D): Thermo Fisher Scientific Inc.; and real-time fluorescence quantitative PCR instrument: Life Sciences of Analytik Jena AG, Germany.

Example 1

Design and Synthesis of Different Types of Oligonucleotide Chain Substrates Related to the Experiment:

Various types of oligonucleotide chain substrates were designed, including linear chain and stem-loop structures with different lengths and different adenine contents, and the 5' terminus and the 3' terminus of all the oligonucleotide chains were labeled with FAM fluorescent group and BHQ1 quenching group and were synthesized by GenScript Biotech Corporation. The sequence information of different types of oligonucleotide chain substrates is shown in Table 1.

TABLE 1

Sequence information of different types of oligonucleotide chain substrates

| Name | Sequence | Note |
|---|---|---|
| DNA15A | FAM-AAAAAAAAAAAAAAA-BHQ1 | Linear chain structure |
| RNA15A | FAM-AAAAAAAAAAAAAAA-BHQ1 | Linear chain structure |
| DNA15(A) | FAM-GCTCTGCAGTCGCTG-BHQ1 | The linear chain structure only contains one A |
| RNA15(A) | FAM-GCUCUGCAGUCGCUG-BHQ1 | The linear chain structure only contains one A |
| DNA32A-6GA | FAM-TATATATATAGAGAGAGAGATATATATATA-BHQ1 | The stem of the stem-loop structure contains A |
| RNA32A-6GA | FAM-UAUAUAUAUAGAGAGAGAGAUAUAUAUAUA-BHQ1 | The stem of the stem-loop structure contains A |
| DNA32-6GA | FAM-GCGCGCGCGCGAGAGAGAGAGCGCGCGCGC-BHQ1 | The stem of the stem-loop structure does not contain A |
| RNA32-6GA | FAM-GCGCGCGCGCGAGAGAGAGAGCGCGCGCGC-BHQ1 | The stem of the stem-loop structure does not contain A |

Example 2

Verification of AP Lyase Activity:

100 µg/mL, 10 µg/mL and 1 µg/mL of RT were used to act on the different types of oligonucleotide chain substrates designed in Example 1 (see Table 1 for details), and sterile water was taken as a negative control, reactions were performed at 37° C. and 55° C. to explore whether RT had AP lyase activity. The reaction system was 30 µL in volume and was composed of 6 µL of ammonium formate buffer solution, 6 µL of BSA solution, 6 µL of substrate, 6 µL of AT and 6 µL of sterile water. The used buffer solution was 20 mM ammonium formate buffer solution, the final concentration of the substrate was 10 µM, and the final concentration of BSA was 50 µg/mL. After the reaction system was prepared and reacted, the reaction system was placed in a qPCR instrument for incubation at a constant temperature, the instrument was set as FAM channel fluorescence signal acquisition, and fluorescence signal value detection was performed in the first step for 72 cycles, wherein the cycle conditions were 5 s in the first step and 9 min in the second step for 55 s. After the reaction was completed, the original data obtained by the detection of the instrument was processed, and the difference between the change in the fluorescence signal value after three different concentrations of AT acted on the same substrate after 72 cycles and the change in the fluorescence signal value of the negative control was compared.

Figure 1B:
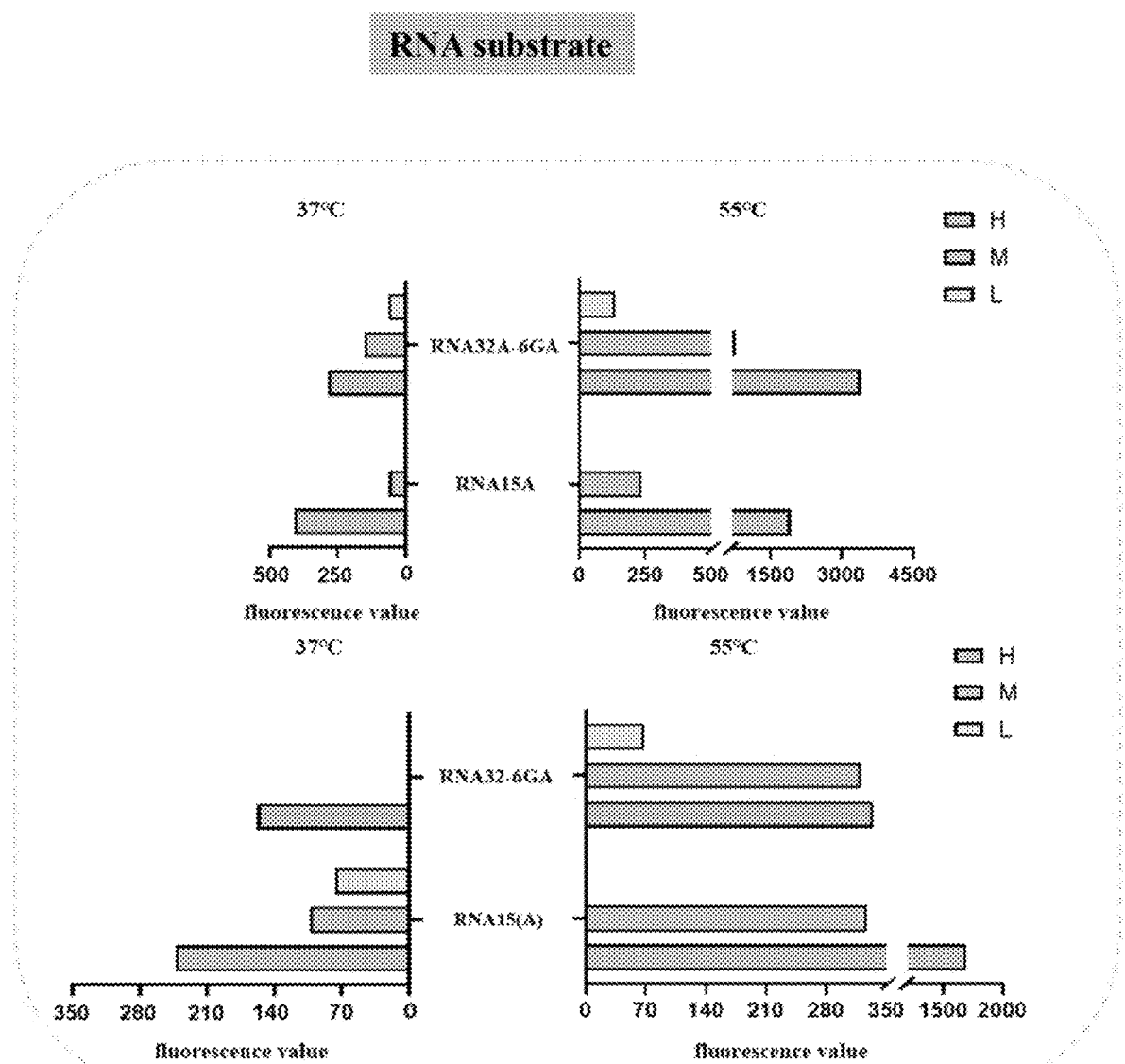
Figure 2A:
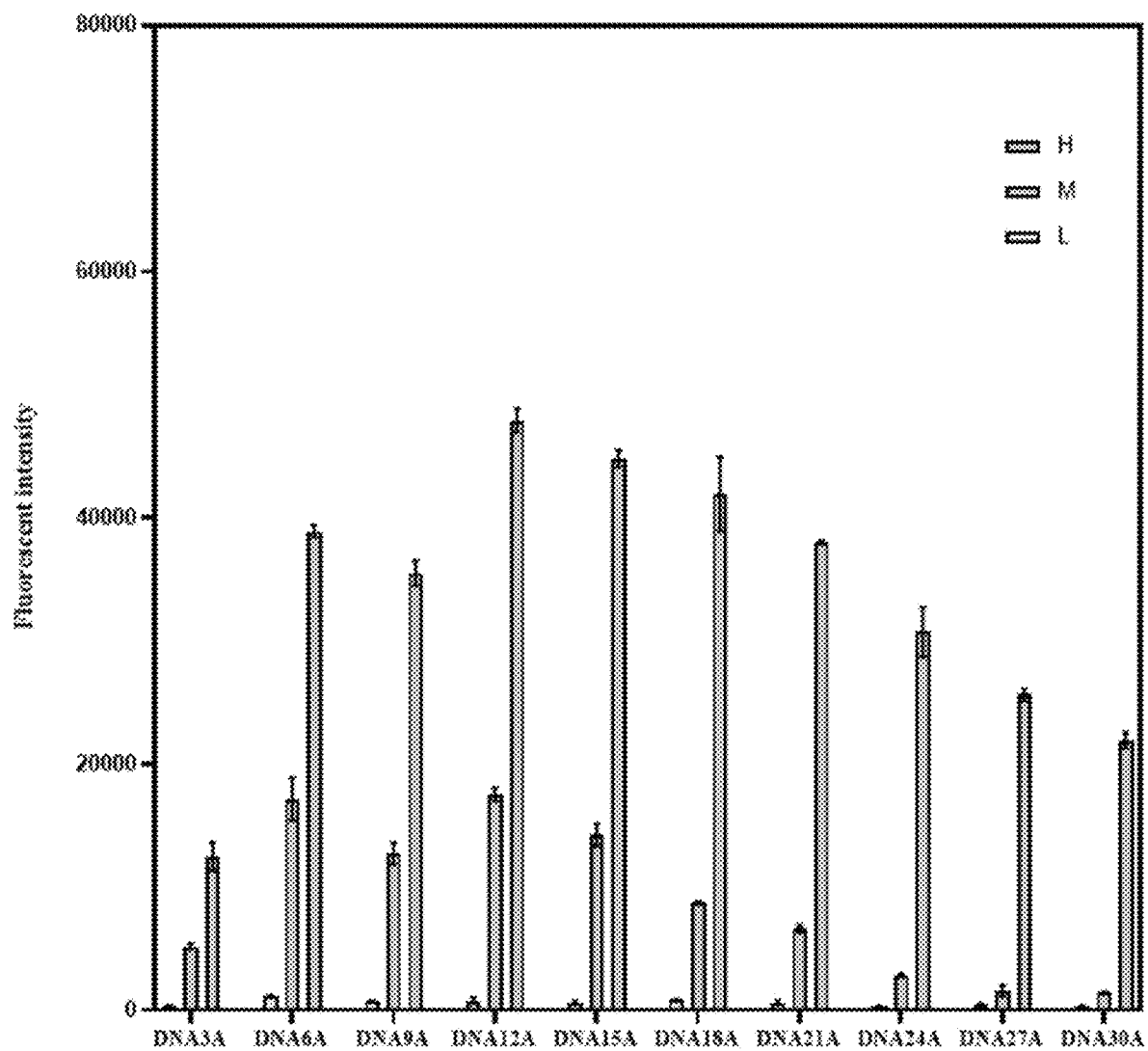
FIGS. 2A-2F are graphs showing the reaction results of various types of substrates (note: H, 100 µg/mL; M, 10 µg/mL; L, 1 µg/mL)
Figure 2B:
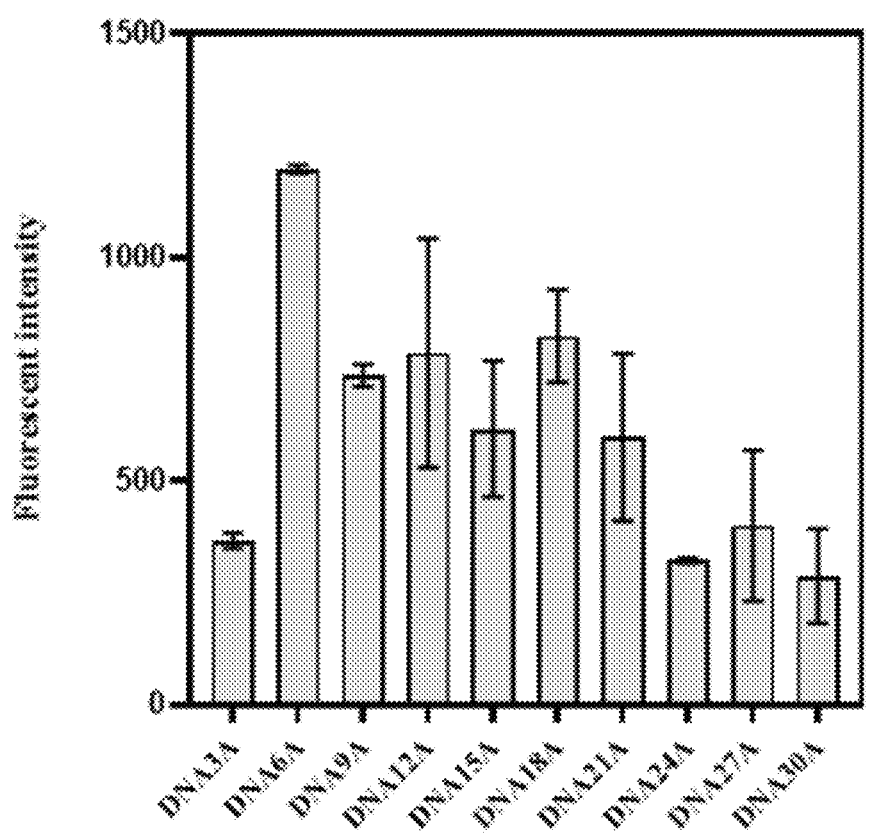
Figure 2C:
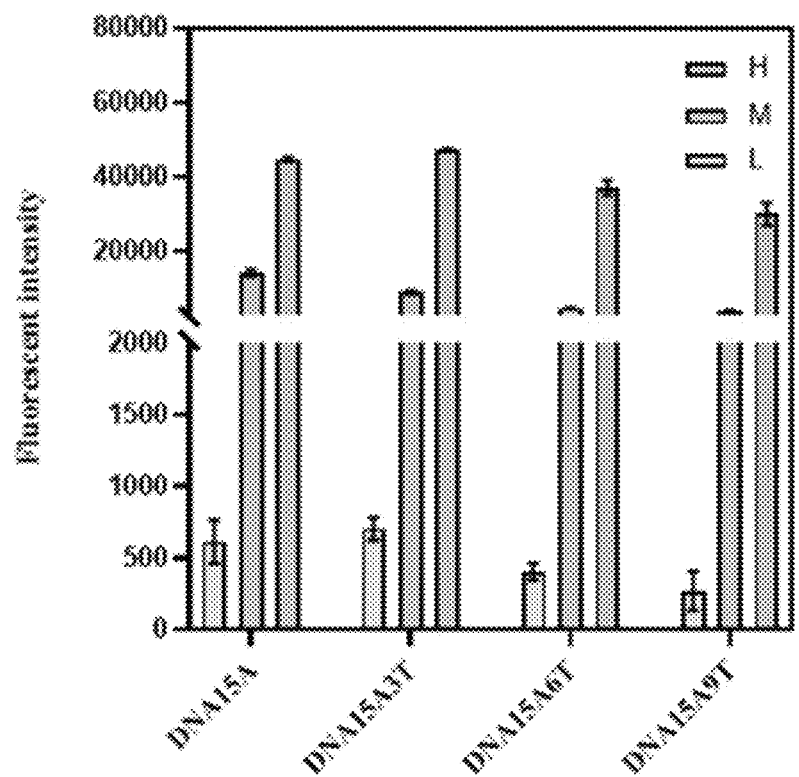
Figure 2D:
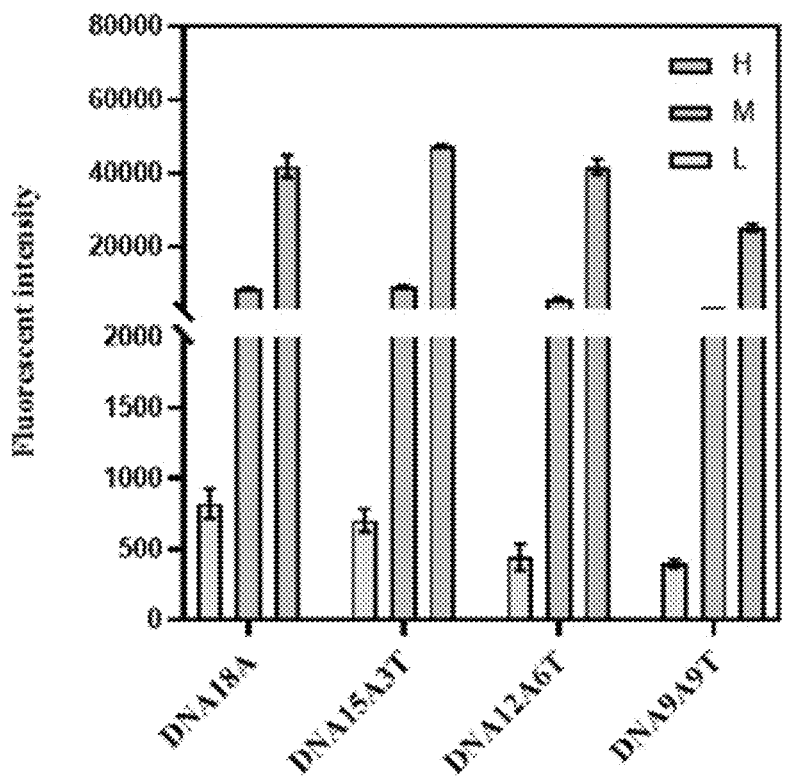
Figure 2E:
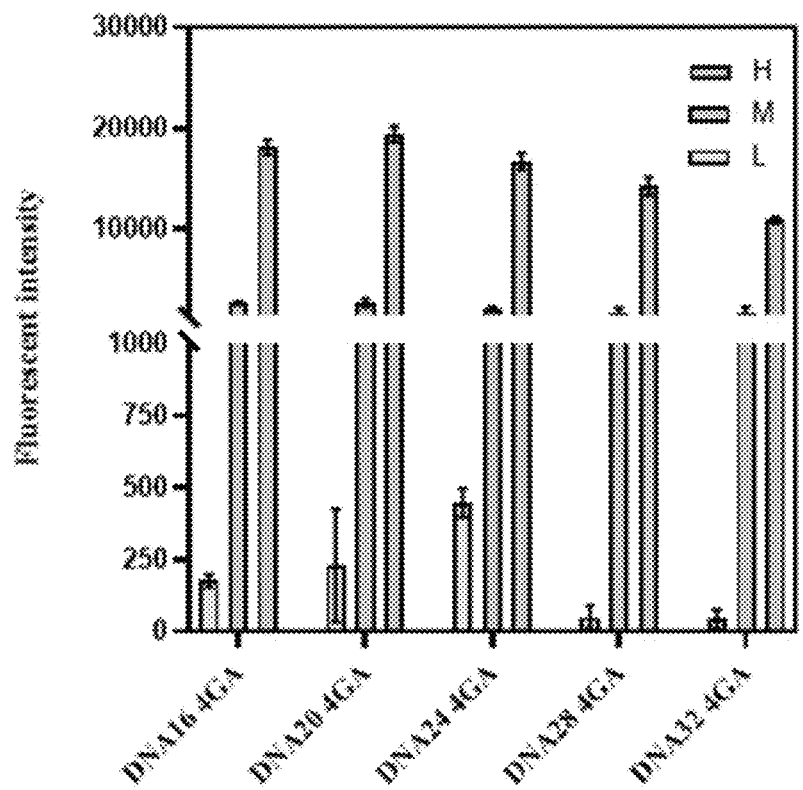
Figure 2F:
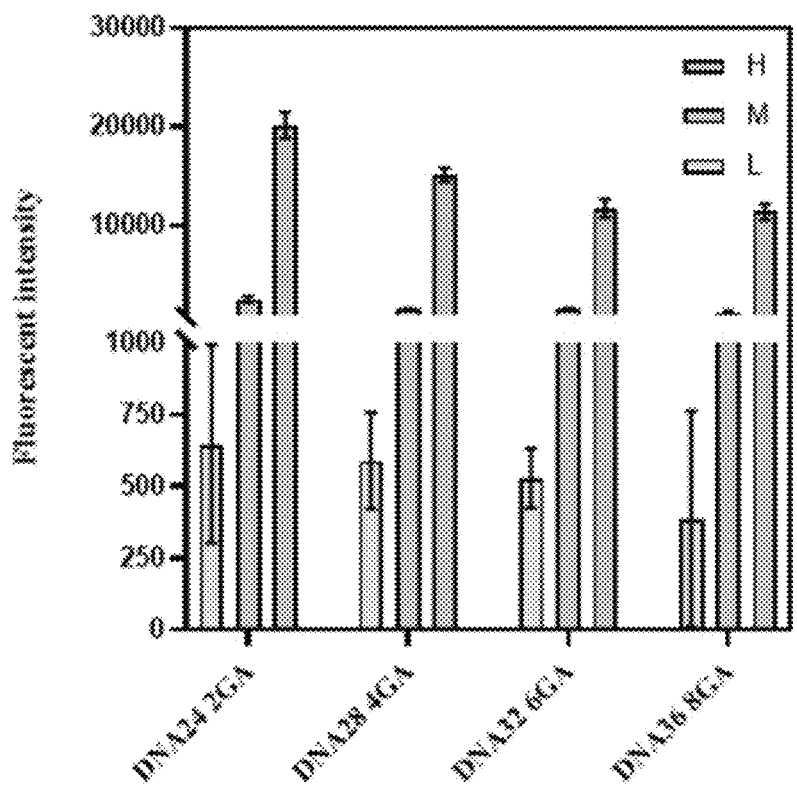
Figure 3:
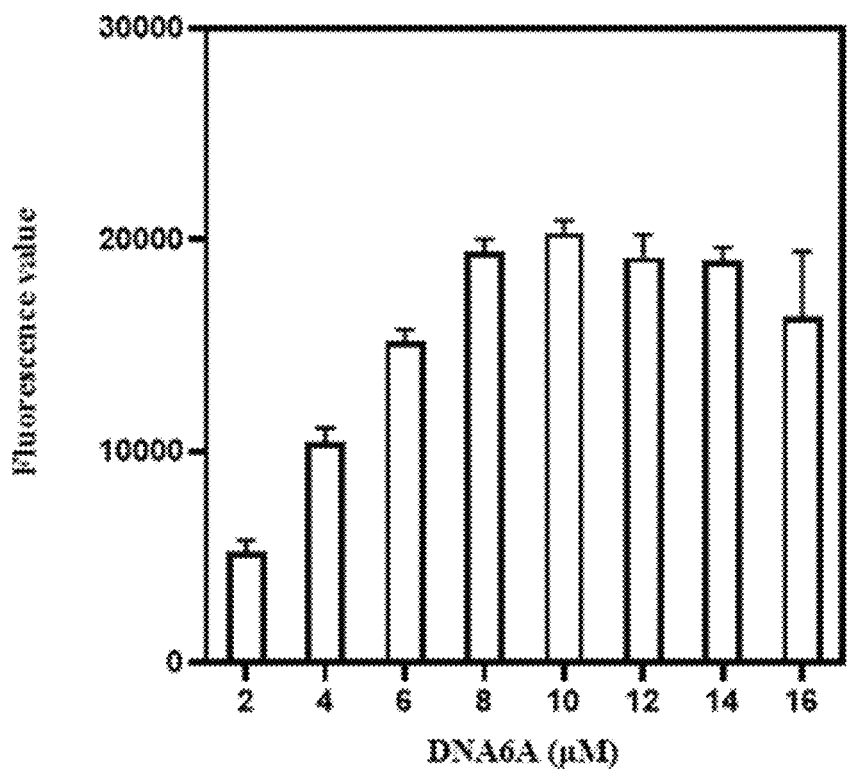
FIG. 3 is a graph showing the results of different reaction concentrations of DNA6A.
Figure 4:
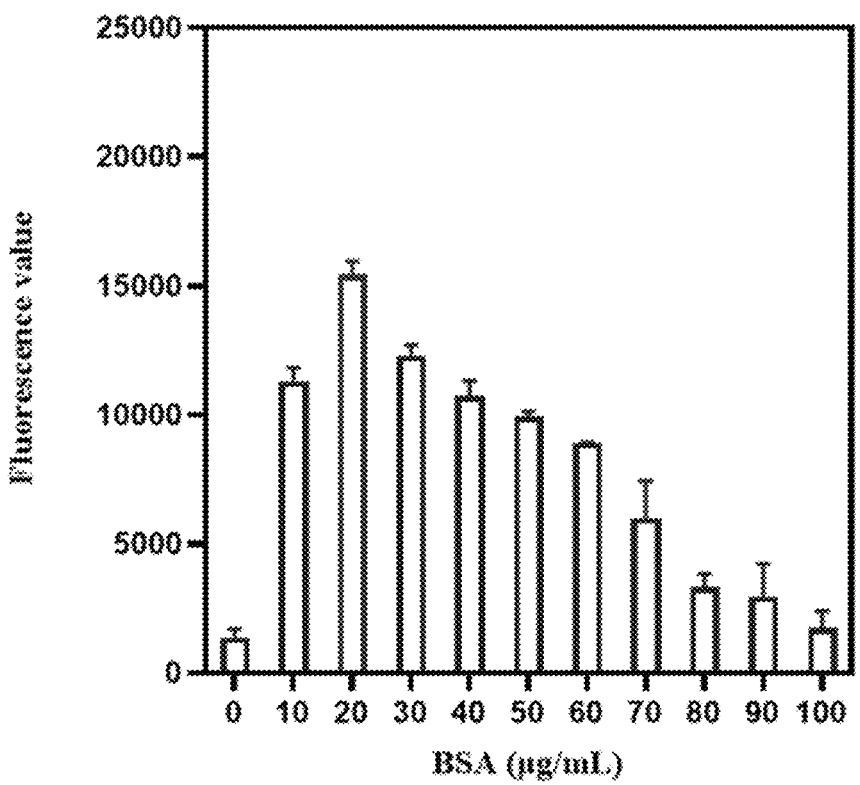
FIG. 4 is a graph showing the results of different reaction concentrations of BSA.
Figure 5A:
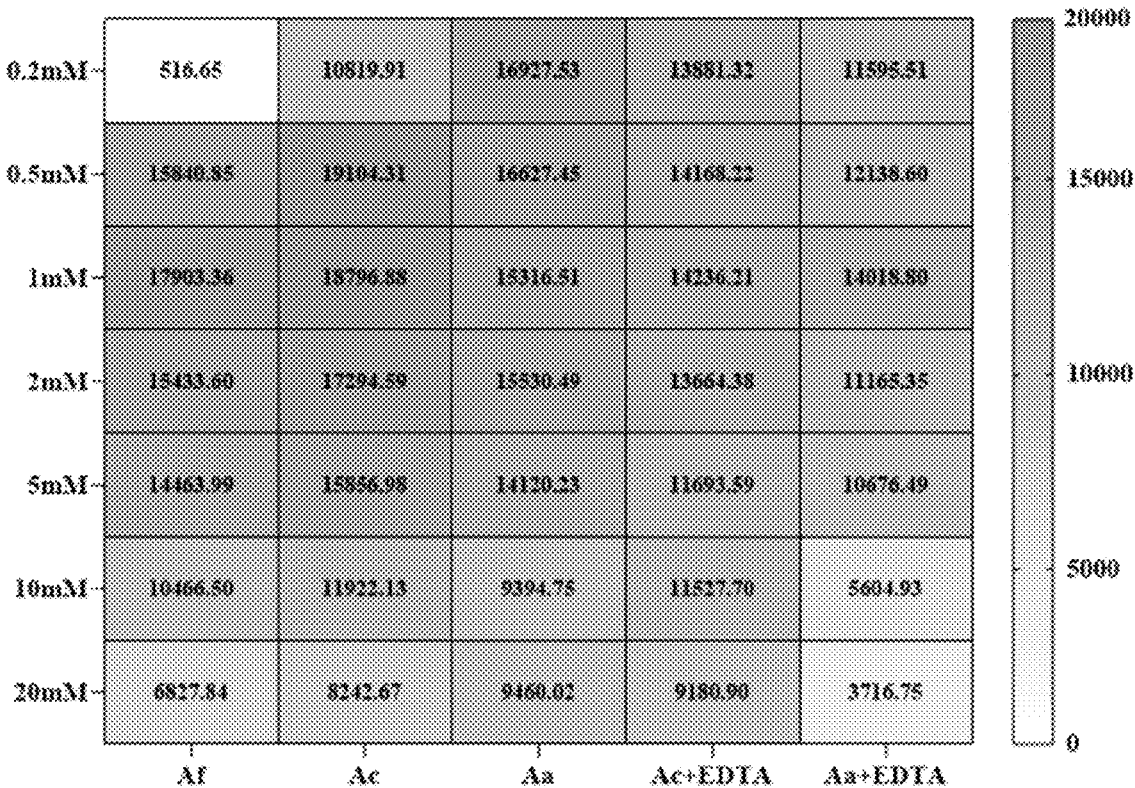
FIGS. 5A-5B are graphs showing the reaction results of different buffer solutions and optimal buffer solutions at different pH values.
Figure 5B:
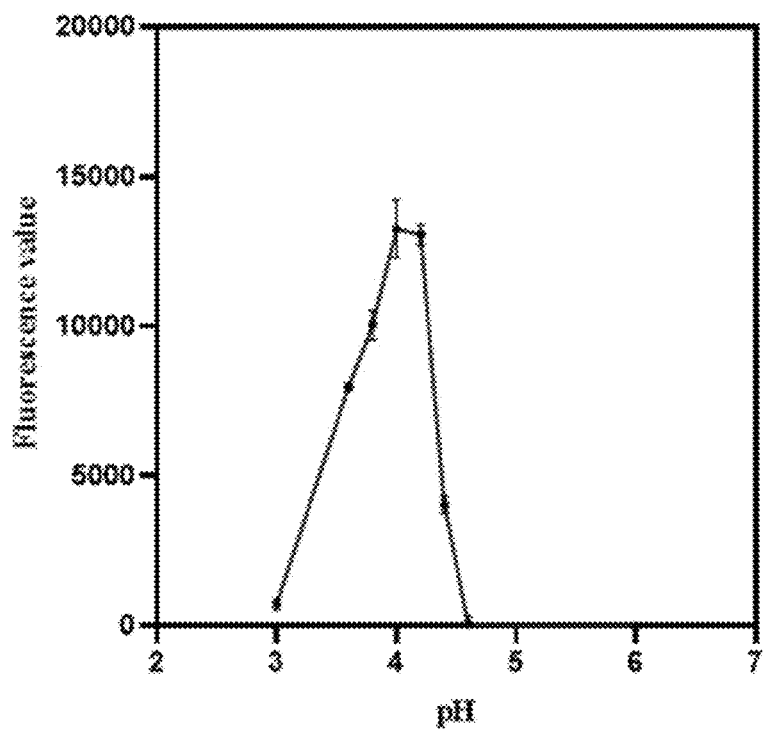

The experimental results are shown in FIGS. 1A-1B. It can be seen from FIGS. 1A-1B that RT can act on single-stranded DNA substrates as well as single-stranded RNA substrates, both of which can cleave the corresponding substrate at the formed AP site; under the same reaction conditions, the response value of the fluorescence signal of the RT acting on the single-stranded DNA substrate is significantly higher than that of the corresponding single-stranded RNA substrate, and the more the adenine contained in the single-stranded DNA substrate, the higher the response value of the generated fluorescence signal; and when the RT acts on the same substrate, the response value of the fluorescence signal at the temperature of 55° C. is significantly higher than that at the temperature of 37° C.

Example 3

Optimization of Reaction Substrates:

A DNA substrate was selected as an optimization object, and 25 µg/mL RT was used to act on different types of stem-loop structures and linear single-stranded DNA substrates (specific sequence information is shown in Table 2), and sterile water was used as a negative control. The reactions were performed at 55° C. The reaction system was 5 µL in volume and was composed of 1 µL of ammonium formate buffer solution, 1 µL of BSA solution, 1 µL of substrate, 1 µL of AT and 1 µL of sterile water. The final concentration of the ammonium formate buffer solution was 20 mM, the final concentration of the substrate was 10 µM, and the final concentration of the BSA was 50 µg/mL. After the reaction system was prepared and reacted, the reaction system was placed in a qPCR instrument for incubation at a constant temperature, the instrument was set as FAM channel fluorescence signal acquisition, and fluorescence signal value detection was performed in the first step for 4 cycles, wherein the cycle conditions were 5 s in the first step and 9 min in the second step for 55 s. After the reaction was completed, the original data obtained by the detection of the instrument was processed, the difference between the change in the fluorescence signal value after three different concentrations of RT acted on the same substrate after 4 cycles and the change in the fluorescence signal value of the negative control was compared, and the optimal reaction substrate was selected.

The experimental results are shown in FIGS. 2A-2F.

TABLE 2

Sequence information of single-stranded DNA substrates of different lengths for substrate optimization

| Name | Sequence | Note |
| --- | --- | --- |
| DNA3A | FAM-AAA-BHQ1 | Linear single-stranded DNA |
| DNA6A | FAM-AAAAAA-BHQ1 | |
| DNA9A | FAM-AAAAAAAAA-BHQ1 | |
| DNA12A | FAM-AAAAAAAAAAAA-BHQ1 | |
| DNA15A | FAM-AAAAAAAAAAAAAAA-BHQ1 | |
| DNA18A | FAM-AAAAAAAAAAAAAAAAAA-BHQ1 | |
| DNA21A | FAM-AAAAAAAAAAAAAAAAAAAAA-BHQ1 | |
| DNA24A | FAM-AAAAAAAAAAAAAAAAAAAAAAAA-BHQ1 | |
| DNA27A | FAM-AAAAAAAAAAAAAAAAAAAAAAAAAAA-BHQ1 | |
| DNA30A | FAM-AAAAAAAAAAAAAAAAAAAAAAAAAAAAAA-BHQ1 | |
| DNA15A3T | FAM-TAAAAAAATAAAAAAAT-BHQ1 | The number of A is unchanged The number of T increases |
| DNA15A6T | FAM-TAAATAAATAAATAAATAAAT-BHQ1 | |
| DNA15A9T | FAM-TAATAATAATAATAATATAAT-BHQ1 | |
| DNA15A3T | FAM-TAAAAAAATAAAAAAAT-BHQ1 | The length is unchanged The number of T increases |
| DNA12A6T | FAM-TAAATAAATAATAAT-BHQ1 | |
| DNA9A9T | FAM-TATATATATATATATAAT-BHQ1 | |
| DNA16-4GA | FAM-TATAGAGAGAGATATA-BHQ1 | Stem-loop structure The ring size is unchanged The stem length increases |
| DNA20-4GA | FAM-TATATAGAGAGAGATATATA-BHQ1 | |
| DNA24-4GA | FAM-TATATATAGAGAGAGATATATATA-BHQ1 | |
| DNA28-4GA | FAM-TATATATATAGAGAGAGATATATATATA-BHQ1 | |
| DNA32-4GA | FAM-TATATATATATAGAGAGAGAGATATATATATATA-BHQ1 | |
| DNA24-2GA | FAM-TATATATATAGAGATATATATATA-BHQ1 | Stem-loop structure The stem length is unchanged The loop size increases |
| DNA28-4GA | FAM-TATATATATAGAGAGAGATATATATATA-BHQ1 | |
| DNA32A-6GA | FAM-TATATATATAGAGAGAGAGAGATATATATATA-BHQ1 | |
| DNA36-8GA | FAM-TATATATATAGAGAGAGAGAGAGAGATATATATATA-BHQ1 | |

It can be seen from FIGS. 2A-2F that DNA6A in the linear single-stranded DNA substrates is the optimal substrate for the reaction.

Example 4

Optimization of Reaction Components:

DNA6A was selected as the optimal reaction substrate, the optimal reaction concentration of the reaction substrate and the optimal reaction concentration of BSA were explored, and the reaction effects of the ammonium formate buffer solution, the ammonium acetate buffer solution, the ammonium citrate buffer solution, the ammonium acetate+EDTA buffer solution and the ammonium citrate+EDTA buffer solution with different concentrations were compared. The substrate concentrations were 2 µM, 4 µM, 6 µM, 8 µM, 10 µM, 12 µM, 14 µM, 16 µM, 18 µM, and 20 µM, and the BSA concentrations were 10 µg/mL, 20 µg/mL, 30 µg/mL, 40 µg/mL, 50 µg/mL, 60 µg/mL, 70 µg/mL, 80 µg/mL, 90 µg/mL, and 100 µg/mL. The concentration gradient of various buffer solutions was 0.2 mM, 0.5 mM, 1 mM, 2 mM, 5 mM, 10 mM, and 20 mM, and the pH was 4.0. After the optimal reaction buffer solution and the reaction concentration thereof were determined, the optimal reaction pH of the buffer solution was explored, including pH 2.15, pH 3, pH 3.6, pH 3.8, pH 4.0, pH 4.2, pH 4.4, pH 4.6, pH 5, pH 6, and pH 7. The sterile water was used as a negative control in all reactions, the reaction temperature was 55° C., the volume of the reaction system was 5 µL, and the system was composed of 1 µL of the buffer solution, 1 µL of the BSA solution, 1 µL of the substrate, 1 µL of RT/sterile water and 1 µL of sterile water. After the reaction system was prepared and reacted, the reaction system was placed in a qPCR instrument for incubation at a constant temperature, the instrument was set as FAM channel fluorescence signal acquisition, and fluorescence signal value detection was performed in the first step for 4 cycles, wherein the cycle conditions were 5 s in the first step and 9 min in the second step for 55 s. After the reaction was completed, the original data obtained by the detection of the instrument was processed, and the difference between the change in the fluorescence signal value after RT acted on the substrate after 4 cycles and the change in the fluorescence signal value of the negative control was compared.

The experimental results are shown in FIGS. 3-5B. It can be seen from FIGS. 3-5B that the optimal reaction concentration of DNA6A is 10 µM, the optimal reaction concentration of BSA is g/mL, the optimal reaction buffer solution is 0.5 mM of the ammonium citrate buffer solution, and the optimal reaction pH value is 4.0.

Example 5

Optimization of Reaction System Volume and Reaction Temperature:

The optimal volume and the optimal reaction temperature of the reaction system were explored. First, 100 µg/mL, 10 µg/mL and 1 µg/mL of RT were used, and sterile water was used as a negative control. The reaction was performed at 55° C., and the reaction system volumes were 5 L, 10 µL, 15 µL, 20 µL, 25 µL, and 30 µL. The system was composed of 0.5 mM of the ammonium citrate buffer solution at the pH value of 4.0, 20 µg/mL of the BSA solution, 10 µM of the substrate, the corresponding concentration of RT and the sterile water. Then, the reaction was performed at 43.4° C., 47° C., 51° C., 55° C., 59° C., 63° C., 67° C. and 70.6° C. using 25 µg/mL of RT and the reaction system volume of 5 µL.

Figure 6:
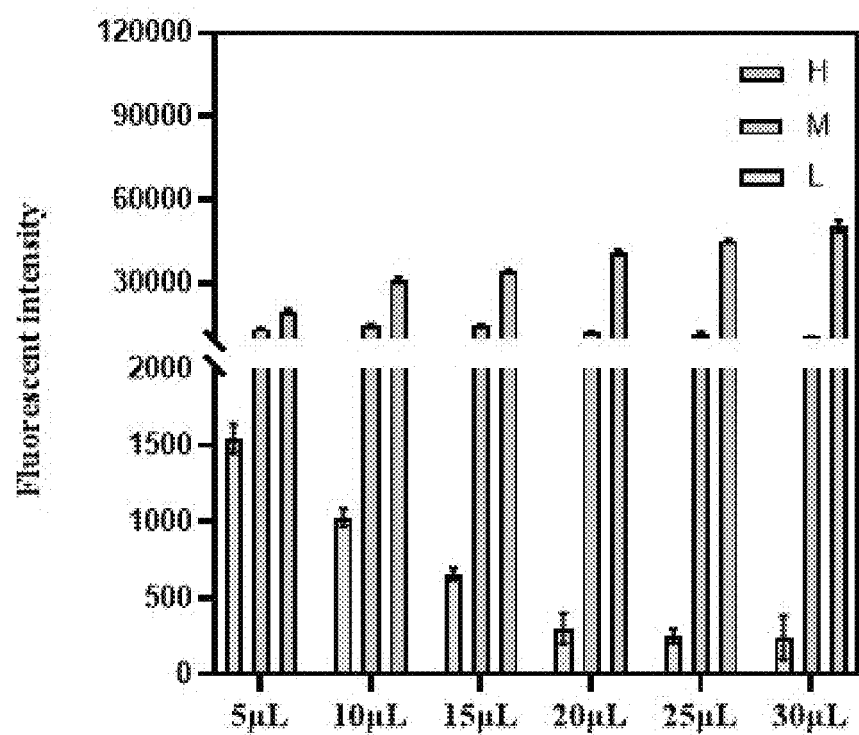
FIG. 6 is a graph showing the reaction results of different reaction system volumes (note: H, 100 µg/mL; M, 10 µg/mL; L, 1 µg/mL)
Figure 7:
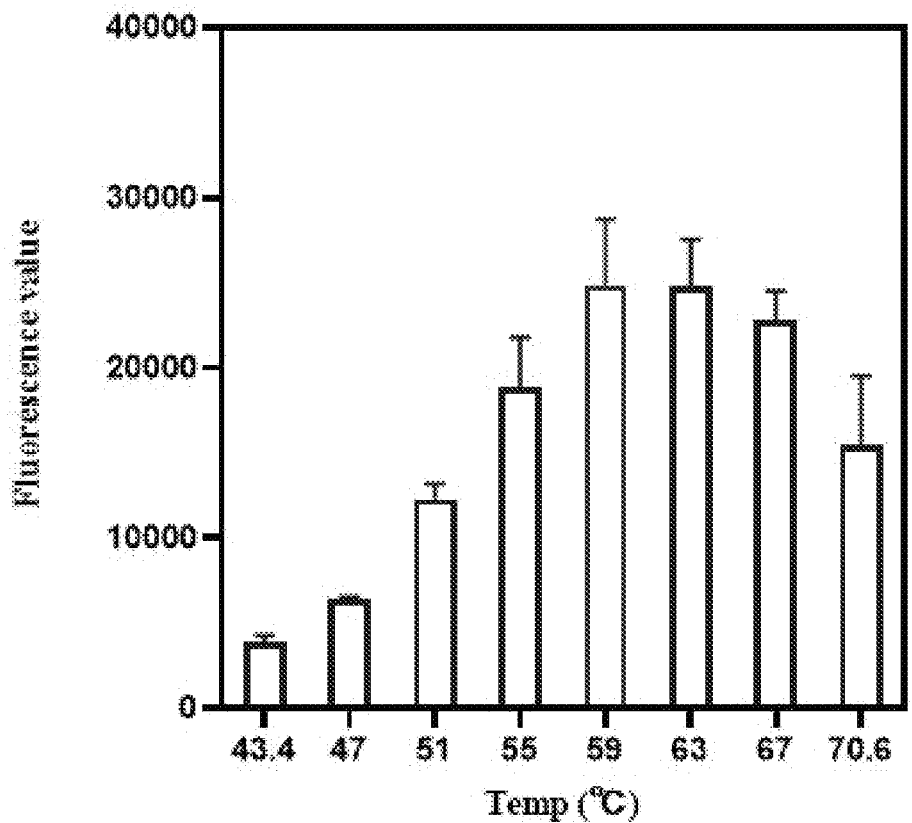
FIG. 7 is a graph showing the reaction results at different reaction temperatures.

The experimental results are shown in FIGS. 6-7. It can be seen from FIGS. 6-7 that when the reaction system volume is 5 µL, the fluorescence signal value in the RT reaction at a low concentration has the highest response intensity, and therefore, 5 µL is selected as the optimal reaction system volume. When the reaction temperature is 59° C., the fluorescence signal value has the highest intensity, and therefore, 59° C. is selected as the optimal reaction temperature.

Example 6

Optimization of Detection Sensitivity after Direct Addition of the Samples into the Reaction System:

The sample enrichment was performed without using antibody-coated magnetic beads, and the detection sensitivity of the detection method was explored by using an optimized reaction system. The sterile water was used as a negative control, and the reaction was performed at 59° C. The concentrations of RT were set to 3 µg/mL, 2 µg/mL, 1 µg/mL, and 0.5 µg/mL, and the reaction system volume was 5 µL, and the system was composed of 1 µL of 0.5 mM ammonium citrate buffer solution at pH 4.0, 1 µL of 20 µg/mL BSA solution, 1 µL of 10 µM substrate DNA6A, 1 µL of RT/sterile water, and 1 µL of sterile water. After the reaction system was prepared and reacted, the reaction system was placed in a qPCR instrument for incubation at a constant temperature, the instrument was set as FAM channel fluorescence signal acquisition, and fluorescence signal value detection was performed in the first step for 4 cycles, wherein the cycle conditions were 5 s in the first step and 9 min in the second step for 55 s. After the reaction was completed, the original data obtained by the detection of the instrument was processed, and the final fluorescence signal value after different concentrations of RT acted on the same substrate after 4 cycles was compared with the final fluorescence signal value of the negative control. The sample was judged as a positive sample when the final fluorescence signal value of the sample was greater than the final fluorescence signal value of the negative control by +3 times of the standard deviation.

Figure 8:
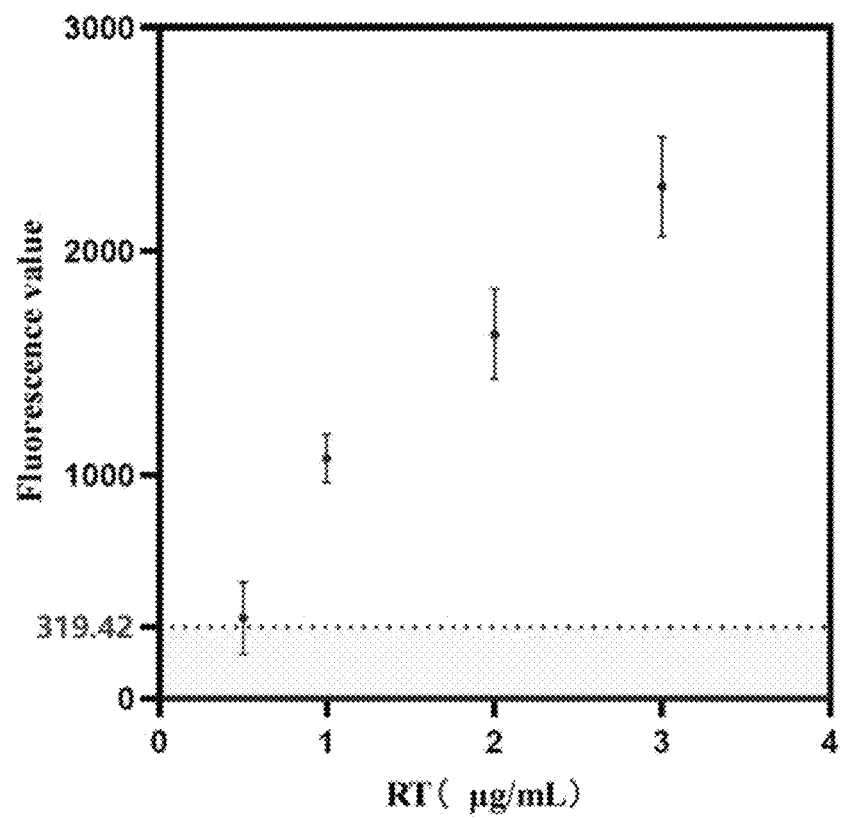
FIG. 8 is a graph showing the detection sensitivity results of RT without adding magnetic beads.

The experimental results are shown in FIG. 8. It can be seen from FIG. 8 that the detection sensitivity of RT is 0.5 µg/mL.

Example 7

Optimization of Detection Sensitivity of the Reaction System after Sample Enrichment by Antibody-Coated Magnetic Beads:

The sample enrichment was performed using antibody-coated magnetic beads, the coating amount of the antibody and the magnetic beads was 25 µg of the antibody-coated 1 mg of the magnetic beads, and 50 µg of magnetic beads was used for each sample. The sample volume was 500 µL. After incubation with the corresponding magnetic beads at room temperature for 1 h, the sample was adsorbed by a magnetic rack for 1 min, and the supernatant was removed. The optimized reaction system was then added, pipetted gently and incubated at 59° C. for 40 min. The concentrations of RT were set to 400 ng/mL, 300 ng/mL, 200 ng/mL, 100 ng/mL, 20 ng/mL, and 10 ng/mL, and sterile water was used as a negative control to explore the reaction system and the detection sensitivity of the detection method. The specificity of the reaction system was verified using 10 µg/mL of AT samples.

Figure 9:
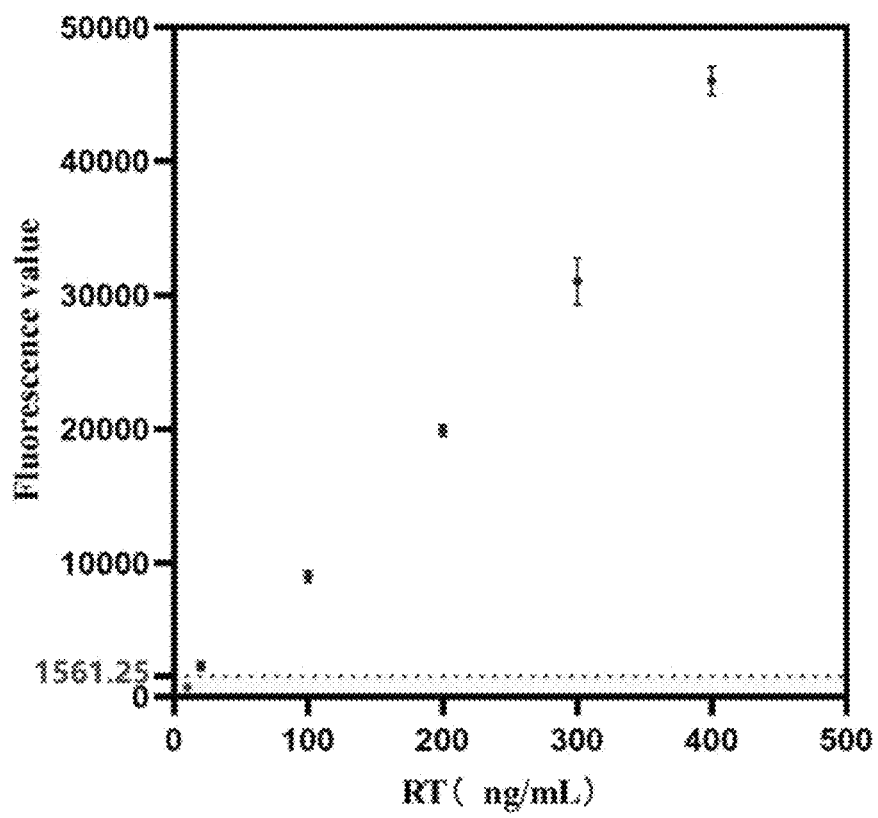
FIG. 9 is a graph showing the detection sensitivity results of RT with adding magnetic beads (note: blue RT 400 ng/mL; yellow RT 100 ng/mL; red RT 20 ng/mL; green negative control)
Figure 10:
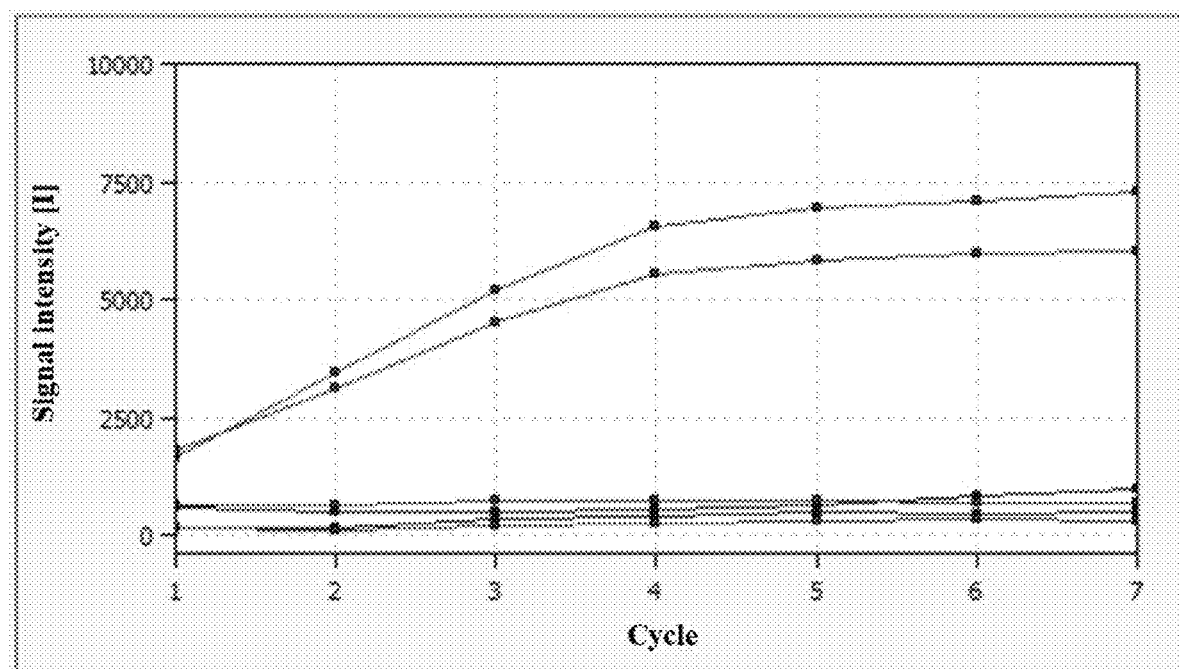
FIG. 10 is a graph showing the results of specificity verification (note: red: RT 10 µg/mL; green: AT 10 µg/mL; blue: negative control).

The experimental results are shown in FIGS. 9-10. It can be seen from FIGS. 9-10 that the detection method has good specificity, no cross reaction with AT occurs (FIG. 10), and the detection sensitivity can reach 20 ng/mL, which is about 25 times higher than that before the magnetic beads are used.

It can be seen from the above examples that the reaction system of the present invention is 1 µL of 0.5 mM ammonium citrate buffer solution, 1 µL of 20 µg/mL BSA solution, 1 µL of 10 µM DNA6A substrate, 1 µL of AT and 1 µL of sterile water, and when the sample is directly added to the reaction system, the detection can be completed by constant-temperature incubation at pH 4.0 and 59° C. for 40 min. The method can reach the sensitivity of 0.5 µg/mL, the detection after enrichment using antibody-coated magnetic beads can reach the sensitivity of 20 ng/mL with a strong specificity, and no cross reaction exists between the toxin sample and abrin toxin.

The above descriptions are only preferred embodiments of the present invention. It should be noted that those of ordinary skill in the art can also make several improvements and modifications without departing from the principle of the present invention, and such improvements and modifications shall fall within the protection scope of the present invention.

---

What is claimed is:

1. A detection method for ricin toxin, comprising the following steps:
   subjecting an adenine-containing oligonucleotide chain substrate labeled with a fluorescein (FAM) fluorescent group and a Black Hole Quencher 1 (BHQ1) quenching group, a buffer solution, a bovine serum albumin (BSA) solution, a to-be-detected sample, and sterile water to a reaction to obtain a product,
   incubating the product at a constant temperature between 55 and 70° C.,
   detecting a fluorescence signal value 2-5 times to obtain final fluorescence signal values, and
   determining whether the ricin toxin exists based on a difference between an average value of final fluorescence signal values and an average value of final fluorescence signal values of a negative control;
   wherein the adenine-containing oligonucleotide chain substrate is a single-stranded DNA sequence consisting of SEQ ID NO: 10 (DNA6A) with a 5' terminus labeled with the FAM fluorescent group and a 3' terminus labeled with the BHQ1 quenching group; the adenine-containing oligonucleotide chain substrate has a final concentration of 6-16 μM;
   the buffer solution is an ammonium formate buffer solution, an ammonium acetate buffer solution, an ammonium citrate buffer solution, an ammonium acetate and ethylene diamine tetraacetic acid (EDTA) buffer solution, or an ammonium citrate and EDTA buffer solution;
   the reaction is performed at a pH value of 3.8-4.6; and
   the to-be-detected sample is enriched by using antibody-coated magnetic beads, wherein antibodies for coating the magnetic beads are specific for ricin toxin.

2. The detection method according to claim 1, wherein an amount of the adenine-containing oligonucleotide chain substrate labeled with the FAM fluorescent group and the BHQ1 quenching group, the buffer solution, the BSA solution, the to-be-detected sample, and the sterile water is 0.5-6 μL, respectively.

3. The detection method according to claim 1, wherein an amount of the antibodies for coating the magnetic beads is 20-30 μg per 0.5-2 mg of the magnetic beads.

4. The detection method according to claim 1, wherein the ammonium formate buffer solution, the ammonium acetate buffer solution, and the ammonium citrate buffer solution have a final concentration of 0.2-20 mM, respectively; in the ammonium acetate and EDTA buffer solution, ammonium acetate has a final concentration of 0.2-20 mM, and EDTA has a final concentration of 0.2-0.8 mM; in the ammonium citrate and EDTA buffer solution, ammonium citrate has a final concentration of 0.2-20 mM, and EDTA has a final concentration of 0.2-0.8 mM; and the BSA solution has a final concentration of 10-100 μg/mL.

5. The detection method according to claim 1, wherein the step of incubating the product is performed for 30-50 min.

6. The detection method according to claim 1, wherein the to-be-detected sample is judged as a positive sample when the average value of the final fluorescence signal values is greater than the average value of the final fluorescence signal values of the negative control by +3 times standard deviation.

* * * * *